(12) United States Patent
Fogarty et al.

(10) Patent No.: US 6,491,719 B1
(45) Date of Patent: *Dec. 10, 2002

(54) TUBULAR ENDOLUMINAR PROSTHESIS HAVING OBLIQUE ENDS

(75) Inventors: Thomas J. Fogarty, Portola Valley, CA (US); Jay A. Lenker, Los Altos Hills, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/088,811

(22) Filed: Jun. 2, 1998

Related U.S. Application Data (63) Continuation of application No. 08/744,130, filed on Nov. 5, 1996, now Pat. No. 5,800,520, which is a continuation of application No. 08/402,435, filed on Mar. 10, 1995, now abandoned.

(51) Int. Cl.⁷ ................................................. A61F 2/06
(52) U.S. Cl. ..................................................... 623/1.37
(58) Field of Search ............................. 623/1.37, 1.15, 623/1.31

(56) References Cited

U.S. PATENT DOCUMENTS

| | | | |
|---|---|---|---|
| 3,155,095 A | 11/1964 | Brown ........................ 128/334 |
| 3,833,940 A | 9/1974 | Hartenbach ........................ 3/1 |
| 4,441,215 A | 4/1984 | Kaster ............................ 3/1.4 |
| 4,830,003 A | 5/1989 | Wolff et al. .................. 128/343 |
| 4,877,030 A | 10/1989 | Beck et al. .................. 128/343 |
| 5,037,427 A | 8/1991 | Harada et al. ............... 606/108 |
| 5,041,126 A | 8/1991 | Gianturco .................... 606/195 |
| 5,102,417 A | 4/1992 | Palmaz ........................ 606/195 |
| 5,123,917 A | 6/1992 | Lee ................................. 623/1 |
| 5,127,919 A | 7/1992 | Ibrahim et al. ................. 623/1 |
| 5,156,619 A | 10/1992 | Ehrenfeld ....................... 623/1 |
| 5,156,620 A | 10/1992 | Pigott ............................. 623/1 |
| 5,167,614 A | 12/1992 | Tessmann et al. .............. 604/8 |
| 5,183,085 A | 2/1993 | Timmermanns ............... 140/89 |
| 5,211,658 A | 5/1993 | Clouse ........................... 623/1 |
| 5,269,802 A | 12/1993 | Garber ......................... 606/191 |
| 5,282,824 A * | 2/1994 | Gianturco ....................... 623/1 |
| 5,282,860 A | 2/1994 | Matsuno et al. ............... 623/12 |
| 5,304,200 A | 4/1994 | Spaulding .................... 606/198 |
| 5,342,387 A * | 8/1994 | Summers ........................ 623/1 |
| 5,395,390 A | 3/1995 | Simon et al. ................. 606/198 |
| 5,507,767 A | 4/1996 | Maeda et al. ................ 606/198 |
| 5,514,178 A | 5/1996 | Torchio ........................ 623/12 |
| 5,569,295 A | 10/1996 | Lam ............................ 606/198 |
| 5,591,222 A | 1/1997 | Susawa et al. ................. 623/1 |
| 5,607,445 A | 3/1997 | Summers ..................... 606/198 |
| 5,632,771 A | 5/1997 | Boatman et al. ............... 623/1 |
| 5,667,486 A | 9/1997 | Mikulich et al. ............... 604/8 |
| 5,800,520 A * | 9/1998 | Fogarty et al. ............. 623/1.37 |
| 5,893,887 A * | 4/1999 | Jayaraman ................. 623/1.37 |
| 6,001,124 A * | 12/1999 | Bachinski .................. 623/1.37 |

FOREIGN PATENT DOCUMENTS

| | | | |
|---|---|---|---|
| DE | 40 32 759 | 4/1992 | ............. A61F/2/04 |
| EP | 566807 | 10/1993 | ............. A61F/2/06 |
| FR | 2 667 783 A1 | 4/1992 | ............. A61F/2/04 |
| WO | 97/07752 | * 3/1977 | |

* cited by examiner

Primary Examiner—Bruce Snow
(74) Attorney, Agent, or Firm—Sterne, Kessler, Goldstein & Fox P.L.L.C.

(57) ABSTRACT

An intraluminar prosthesis which includes a tubular member having at least one end which is at an oblique angle to the lumen. The prosthesis is inserted into a body lumen, such as a blood vessel, while compressed. The prosthesis is expanded within the lumen, and the oblique end of the prosthesis contacts the lumen at an oblique angle. This oblique angle reduces the stenotic effects of hyperplasia which generally occurs at the ends of intraluminal prostheses.

19 Claims, 8 Drawing Sheets

TUBULAR ENDOLUMINAR PROSTHESIS HAVING OBLIQUE ENDS

This is a continuation of application Ser. No. 08/744,130, filed Nov. 5, 1996, now U.S. Pat. No. 5,800,520, which is a continuation of Ser. No. 08/402,435, filed Mar. 10, 1995, now abandoned.

BACKGROUND OF THE INVENTION

1. Field of the Invention

The present invention relates generally to intraluminal prostheses and methods for their use. More particularly, the present invention relates to intraluminal grafts and stents having oblique ends to reduce stenosis, and methods for the treatment of defective body lumens using such prostheses.

Vascular diseases amenable to treatment by the devices and methods of the present invention include both occlusive diseases and aneurysms. Occlusive diseases are characterized by the build-up of stenotic materials in the affected blood vessel, resulting in partial or total occlusion of the blood vessel lumen.

Vascular aneurysms are the result of abnormal dilation of a blood vessel, usually resulting from disease and/or genetic predisposition which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending distally into one or both of the iliac arteries.

The use of stents is gaining widespread acceptance in the treatment of occlusive diseases. Usually, a stenotic lesion is treated by balloon angioplasty with the simultaneous or subsequent placement of a stent to maintain vessel patency. While holding great promise as an improvement over angioplasty alone, the use of stents can have drawbacks. Of particular concern to the present invention, stents can themselves provide initiation sites for hyperplasia, particularly at each end where the edge of the stent is exposed to the blood vessel lumen. It would therefore be desirable to provide improved stent designs which would lessen problems associated with post-placement hyperplasia.

Aortic aneurysms are most commonly treated in open surgical procedures where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high mortality rate, usually from 3% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular graft placement for the treatment of aneurysms has been proposed. Although very promising, many of the proposed methods and apparatus suffer from other problems. In particular, hyperplasia (excessive cellular proliferation) may occur in blood vessels at the regions adjacent to the ends of an intraluminal graft, stent, or other prosthesis. Such hyperplasia within the lumen of a blood vessel is potentially stenotic, and therefore compromises the therapeutic value of the intraluminal graft.

For these reasons, it would be desirable to provide improved intraluminal prostheses, including both grafts and stents, and methods for treating aneurysms, stenosis, and other conditions using such prostheses. It would be particularly desirable if the prostheses would provide the therapeutic value of existing grafts and stents, but would reduce the stenotic effect of the hyperplasia which generally occurs at the ends of existing structures. It would be further desirable if such prostheses could be inserted and positioned using conventional delivery catheters and methods.

2. Description of the Background Art

Vascular graft prostheses having oblique ends for replacement or bypassing of diseased blood vessels in open surgical procedures are described in U.S. Pat. Nos. 5,127,919 and 4,441,215. An intraluminal graft having a helical end is disclosed in U.S. Pat. No. 5,037,427. Intraluminal grafts having ends normal to the lumen are disclosed in U.S. Pat. Nos. 5,282,860; 5,211,658; 5,167,614; 5,156,620; 4,877,030; and 4,830,003.

Other designs for intraluminal prostheses are described in copending application Ser. Nos. 08/255,681 and 08/290,021, the full disclosures of which are incorporated herein by reference.

SUMMARY OF THE INVENTION

The present invention provides intraluminal prostheses, including both grafts and stents, for the treatment of disease conditions, particularly aneurysms. The intraluminal prostheses provide a decreased risk of luminal occlusion (as discussed below) and comprise a tubular member which is insertable into a body lumen in a small diameter configuration and which can be expanded within the body lumen to an expanded mode. At least one of the ends of the tubular member will have a terminal edge which is disposed at least partially at an oblique angle relative to the lumen of the tubular member.

The intraluminal prostheses may be self-expanding, expandable by the application of a radially outward internal force, or a combination thereof. Self-expanding prostheses are typically delivered to a target location within the body lumen in a radially compressed configuration, e.g. within a tube or other constraining structure. Such self-expanding prostheses may be deployed by first positioning at the target location and subsequently releasing the constraint to permit the prosthesis to expand an anchor within the lumen. Expandable prostheses are delivered to the target location without the need for constraint and are deployed by internal radial expansion, usually by inflating a balloon or other expandable structure within the lumen of the prosthesis. Self-expanding prostheses will preferably be constructed from resilient materials, such as spring stainless steel, shape memory alloys, shape memory plastics, elastic (resilient) plastics, and the like. Expandable prostheses will be preferably constructed from malleable materials such as stainless steels, titanium alloys, tantalum alloys, plastics, and the like. Prostheses have both self-expanding and expandable properties and may be constructed from combinations of these materials.

The intraluminal prostheses of the present invention are suitable for a wide variety of therapeutic uses, including stenting of the ureter, urethra, biliary tract, and the like. The devices and methods will also be useful for the creation of temporary or long term lumens, such as the formation of fistulas. The present invention will find its greatest use, however, in the placement of endovascular grafts into blood vessels for the treatment of abdominal and other aneurysms, vascular stenoses, and the like.

The present intraluminal prostheses provide significant advantages over previously proposed designs, particularly for vascular uses. Any hyperplasia which occurs at the oblique ends of the present invention will occupy an oblique region of the lumen in which the present prosthesis is positioned. Although the total volume of hyperplasia may be the same or greater, the resulting occlusion is reduced, (i.e. effective residual lumen area is increased) because the hyperplasia is distributed axially over the surface of the lumen. In contrast, conventional prostheses having terminal edges perpendicular to the lumen axis will cause a greater degree of occlusion since the opposed regions of hyperplasia are axially aligned across a perpendicular cross section of the lumen. Thus the stenoses of the present intraluminal prostheses are effectively reduced over previous intraluminal prostheses designs.

An additional advantage results from the ability to orient the prosthesis to avoid blocking branch vessel(s). It will be appreciated that a prosthesis having normal ends must be axially positioned to one side of a branch artery to avoid partial or complete occlusion. This limitation can be a significant problem where there is a limited area of blood vessel wall for anchoring the prosthesis. The oblique end of the present invention allows the prosthesis to be anchored beyond the branch vessel without occlusions by properly turning the prosthesis to avoid blockage. This is a particular benefit in the treatment of aortic aneurysms where the graft may be oriented to avoid the renal arteries.

The present invention also provides graft prostheses which comprise a tubular member as described above and a liner covering at least a part of the inside of the lumen and/or the outside surface of the member. The tubular member is usually perforate, and the liner provides a barrier which permits use as a vascular graft for the treatment of aneurysms. Preferably, the ends of the liner are aligned with or parallel to the terminal edges of the tubular frame. The liner is tied, spot welded, or otherwise secured to the tubular member in such a way that the liner can radially expand with the member. Exemplary liner structures suitable for use with the present invention are described in copending application Ser. No. 08/255,681.

The present invention further comprises methods for treatment of disease conditions, particularly aneurysms and stenoses. The treatment method comprises inserting the intraluminal prosthesis into the body lumen while the prosthesis is in its reduced diameter configuration. The prosthesis is positioned within the diseased portion of the lumen, and is expanded to the expanded configuration, either resiliently or by application of an internal expansion force. The expanded prosthesis includes at least one end which is oblique to the lumen of the prosthesis, whereby any hyperplasia which occurs along the line defined by the oblique end will be axially distributed so that effective occlusion of the body lumen is reduced.

DESCRIPTION OF THE SPECIFIC EMBODIMENT

The present invention provides intraluminal tubular prostheses and methods for their use. The prostheses of the present invention are particularly suitable for use within the vascular system for treatment of aneurysms, stenosis, and other vascular conditions, but are also useful in other body lumens, such as ureter, urethra, biliary tract, gastrointestinal tract, and the like, for the treatment of other conditions which benefit from the introduction of a reinforcing or protective structure in the lumen. The apparatus and methods can also find use in the creation of artificial lumens through solid tissue and structures, such as the placement of a TE fistula via an endoscope. The vascular prostheses will be placed endovascularly. As used herein, "endovascularly" will mean placement by percutaneous or cutdown transluminal procedures (at a location remote from the treatment site) using a catheter. Use of a guidewire and/or guide catheter under fluoroscopic guidance may facilitate placement. The catheters and guidewires may be introduced through conventional access sites to the vascular system, such as through the brachial and subclavian arteries for access to the aorta and through the femoral arteries for access to the aorta or to peripheral and branch blood vessels. Suitable apparatus and methods for the endoluminar placement of the present intraluminal prostheses are describe in copending application Ser. No. 08/290,021.

An intraluminal prosthesis according to the present invention will comprise a tubular member having at least one oblique end. The tubular member is expandable from a small diameter configuration for insertion and positioning, to a larger diameter configuration within the body lumen. Preferably, the tubular member comprises a perforate tubular frame. Such a frame may conveniently be formed in the compressed mode by cutting various patterns in a tube, as discussed hereinbelow. Similar tubular members may also be formed in other ways, for example, as a mesh of metal woven into a tube.

Alternatively, the tubular member comprises a plurality of independent or interconnected structural elements, such as rings, bands, serpentine elements, axial struts, parallel bars, and the like. A variety of analogous structures having perpendicular ends are described in co-pending U.S. Pat. application Ser. No. 08/255,681.

In a further alternative, the tubular member comprises a sheet of biocompatible material which is coiled concentrically. The sheet may again be in the form of a wire mesh, for example, or may instead be substantially impermeable. Such coiled tubular members are expanded within the body lumen by expansion of the coil, usually from a relatively tightly wound coil having a significant overlap, to a larger coil having less, if any, overlap. Again, at least one end of the coil is oblique when the tubular member is in the expanded configuration.

In a still further alternative, the tubular member of the present invention is comprised of one or more helical or spirally wound elements. The expansion of a helical tubular member of the present invention from a small diameter configuration to a larger diameter configuration is most simply an expansion of the helical coil, where the helical coil has an oblique end when in the expanded configuration. The end of such a tubular member is preferably formed such that a side view exists from which the angle between the end and an axis of a lumen is seen as being oblique in one direction; i.e., consistently greater than 90°.

Still other alternative construction methods are available for forming the tubular member of the present prostheses. As a final example, the tubular member may be formed as inner and outer resilient tubular layers which are joined together at a proximal end and a distal end, thereby defining an annular cross-section. The annular passage may then have fluid introduced to expand the outer layer against the body lumen, followed by insertion of a plastic material to hold the tubular member in the expanded configuration. Thus a wide variety of structures are available for the tubular member of the present prosthesis, as described in the patent literature.

Regardless of the form of construction used, the tubular member of the present prosthesis has at least one oblique end. As used herein, an intraluminal prosthesis end is oblique when a side view exists from which a significant portion of a terminal end of the prosthesis is at a substantially oblique angle relative to an axis of a lumen of the prosthesis. Such oblique ends avoid having any single cross-section associated with the entire terminal end of the prosthesis.

The oblique angle of the end of the present prostheses will generally range from 20° to 80°, preferable being in the range from 30° to 60°. The angle selected will vary with the intended use of the prosthesis, with the above ranges being preferred for vascular uses.

It will be recognized that the axis of the lumen, from which the oblique angle is measured, may not be straight, and, in fact, may curve and flex with the body lumen in which it is inserted. Thus the angle may be determined by the tangent of the axis of the lumen at the end of the prosthesis.

The particular form of the oblique ends of the present invention will vary with the form of construction of the tubular member. Obviously, tubular members having ends which are continuous allow a continuous oblique angle to be formed. Preferably, the oblique end of such prostheses are, in fact, formed as a continuous, straight end, thereby directly defining the oblique angle. Tubular members having more complex frame structures may also have continuous ends, where a continuous structural element defines the entire terminal end.

The ends of tubular prostheses formed from a plurality of structural elements may be highly irregular. Nonetheless, such uneven elements can form the oblique ends of the present invention. For example, the length of individual structural members can be varied, defining an oblique end as a series of staggered steps. Alternatively, the ends may be formed in part by uneven structural elements, and in part by continuous structural elements.

The dimensions of the tubular prosthesis will depend on its intended use. Typically, the prostheses will have a length in the range from about 50 mm to 500 mm, preferably from about 80 mm to 200 mm for vascular applications. The expanded diameter will usually be in the range from about 4 mm to 45 mm, preferably being in the range from about 5 mm to 25 mm for vascular applications. While in the compressed mode, the prosthesis will have a diameter in the range from 3 mm to 9 mm, preferably from 4 mm to 6 mm for vascular applications.

The tubular member may optionally be composed of a resilient material, usually metal. Preferred resilient metals include heat and/or shape memory alloys, such as nickel titanium alloys which are commercially available under the trade name Nitinol®. The frames may also be composed of other highly elastic metals, such as MP-35 N, Elgiloy, and the like. In the case of Nitinol® and other memory alloys, the phase transition between austenitic and martensitic states may occur between an introduction temperature, e.g., room temperature (approximately 22° C.), and body temperature (37° C.), to minimize stress on the unexpanded frame and enhance radial expansion of the frame from its radially compressed condition. Expansion can also be achieved based on the highly elastic nature of the alloy, rather than true shape recovery based on phase change.

Alternatively, the tubular member may be composed of a malleable material, such as titanium CP II or 316 L stainless steel, tantalum, or the like. The tubular member can be formed and inserted into a body lumen in a compressed mode, and expanded when in position by an internal expansion force, such as a balloon catheter.

In some cases, it may be desirable to form a tubular member having different elastic or other mechanical properties at different regions along its length. For example, it is possible to heat treat different regions of the tubular member so that some regions possess elastic properties while others become malleable so that they may be deformed by external force. By providing at least one malleable end portion and an elastic (radially compressible) middle portion, the graft can be firmly expanded and implanted by internal balloon expansion force (to anchor the end(s) in the inner wall of the blood vessel) while the middle will remain open due to the elastic nature of the tubular member. Malleable end portions are a particular advantage since they can be expanded with a sufficient force, and re-expanded if necessary, to assure a good seal with the blood vessel wall. Alternatively, the malleable ends could be formed from a different material than that of the middle portion of the tubular member. The use of different materials would be particularly convenient when the tubular member is formed from a plurality of independent bands, where one or more band members at either or both ends could be formed of a malleable metal. Usually, such malleable end(s) will extend over a distance in the range from 5 mm to 50 mm, preferably from 5 mm to 20 mm.

Malleable portions or segments can also be formed in other parts of the tubular member. For example, some circumferentially spaced-apart segments of the tubular member could be malleable while the remaining circumferential segments would be elastic. The member would thus remain elastic but have an added malleability to permit expansion by applying an internal expansion force. Such a construction would be advantageous since it would allow the diameter of the graft or stent structure to be expanded if the initial diameter (which resulted entirely from elastic expansion) were not large enough for any reason. The proportion of elastic material to malleable material in the tubular member can be selected to provide a desired balance between the extent of initial, elastic opening and the availability of additional, malleable opening. Such construction can be achieved by selective heat treatment of portions of a frame composed of a single alloy material, e.g. nickel titanium alloy, or by forming circumferential segments of the frame from different materials having different elastic/malleable properties.

Figure 1:
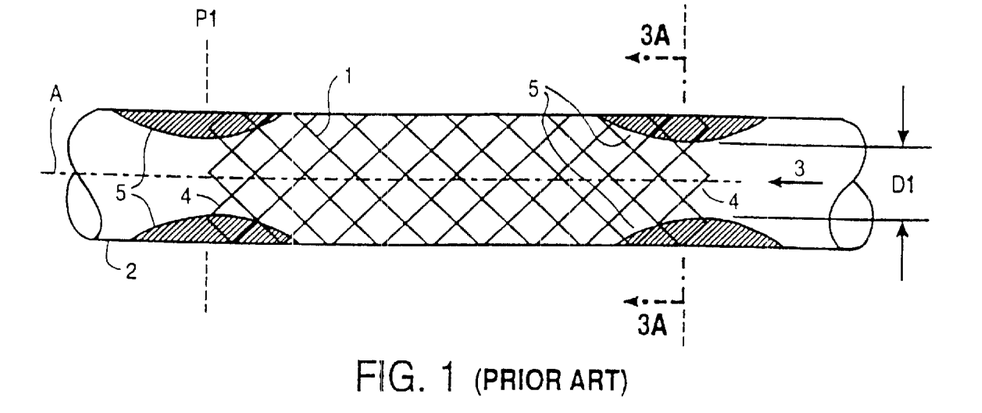
FIG. 1 illustrates a side view of a prior art intraluminal prosthesis having perpendicular ends, shown implanted in a body lumen.

The present invention may be understood by reference to FIGS. 1, 2, 3A, and 3B. FIG. 1 represents a conventional tubular intraluminal prostheses 1 having ends 4 which are generally perpendicular to an axis A through the center of a lumen of the prosthesis 1. The prosthesis 1 is implanted within a body lumen 2. As the ends 4 of the prosthesis 1 are perpendicular to the prosthesis lumen, and as the prosthesis lumen is substantially parallel to the body lumen 2, the ends of the prosthesis 4 contact the body lumen 2 along cross sectional planes P1 and P2 which are generally perpendicular to the axis A. Thus the lumen 2 has a reduced effective diameter D1 at cross sectional planes P1 and P2.

Hyperplasia is a potential side effect of the endoluminal placement of intraluminal prostheses. Hyperplasia of blood vessels and other body lumens causes luminal occlusion, which can substantially reduce the luminal area which remains available after completion of the procedure. Hyperplasia may occur where the ends of a prosthesis contact the inner surface of a body lumen, e.g., the endothelium of blood vessels. Prostheses having perpendicular ends 4 can result in hyperplasia 5, and the effective remaining luminal area is significantly reduced since the regions of hyperplasia on opposite walls of the lumen are directly opposed, i.e. they lie on a cross-sectional plane which is perpendicular to the axis of the lumen, as shown in FIG. 3A.

Figure 2:
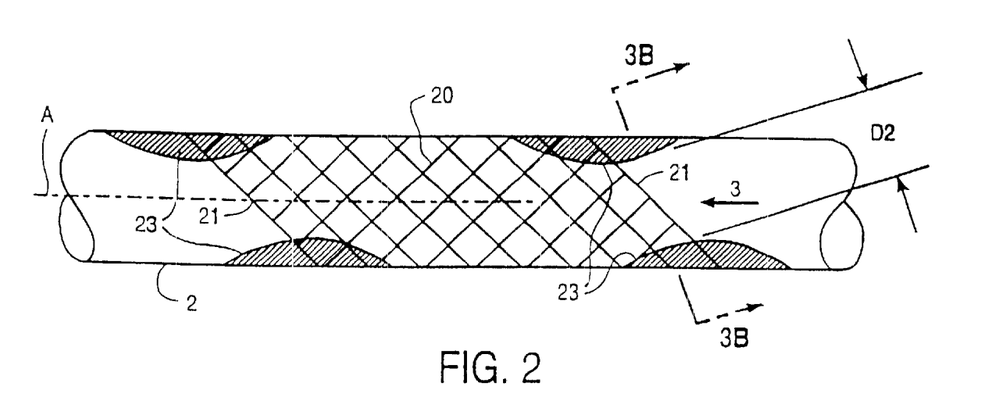
FIG. 2 illustrates a side view of an intraluminal prosthesis according to the present invention, shown implanted in a body lumen.

A prosthesis according to the present invention is shown positioned within a body lumen 2 in FIG. 2. The prosthesis 20 has oblique ends 21 relative to the axis A of the lumen of prosthesis 20, and thus to the body lumen 2. Hyperplasia 23 associated with the present prostheses ends 21 will likewise form an oblique angle to the body lumen 2. Flow 3 through body lumen 2 will encounter the mass of oblique hyperplasia 23 spread the body lumen 2. Flow 3 will be distorted by hyperplasia 23, first flowing over the lower portion, then flowing down under the upper portion. Thus flow 3 encounters the greatest occlusion at an oblique section 3B—3B shown in FIG. 3B. Oblique hyperplasia 23 therefore results in body lumen 2 having effective diameter D2. Note that the distortion of flow 3 and the shape of flow area 24 (See FIG. 3B) will also have some effect on effective diameter D2.

Figure 3A:
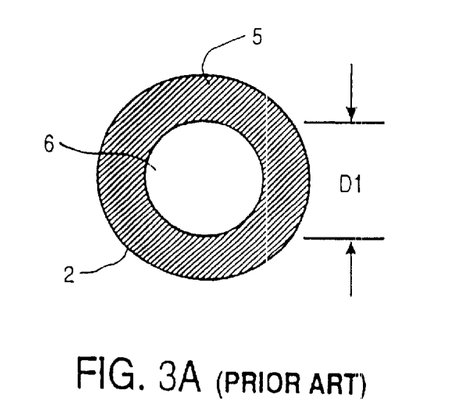
FIGS. 3A and 3B are sectional views of a prior art prosthesis and the present prosthesis implanted in a body lumen, respectively.
Figure 3B:
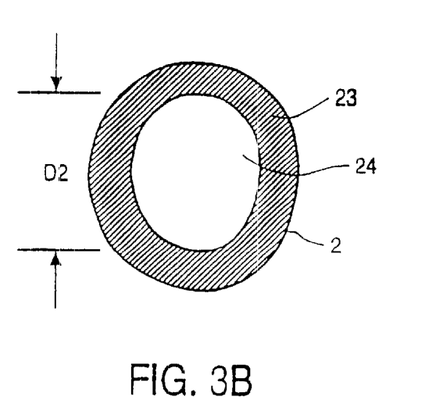

FIGS. 3A and 3B show the reduction in stenosis provided by the present invention. FIG. 3A illustrates the reduced flow area 6 which results from an intraluminal prosthesis 1 with perpendicular ends 4 (see FIG. 1). FIG. 3B illustrates the significantly larger flow area 24 resulting from the present intraluminal prosthesis 21 with oblique ends 21 (see FIG. 2). Thus, stenoses which generally occurs at the ends of intraluminal prostheses are reduced by the oblique ends of the present invention.

Figure 4:
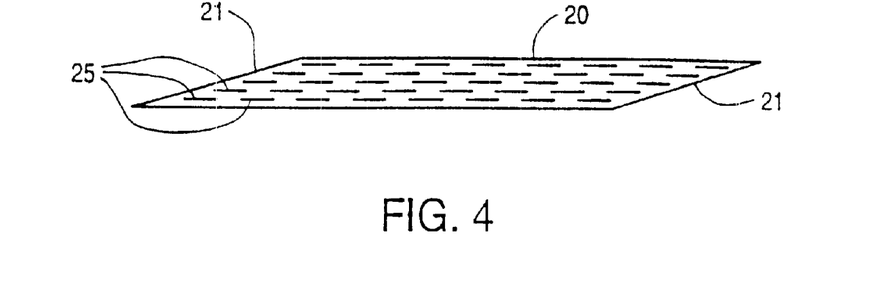
FIG. 4 is a schematic illustration of an embodiment of the present invention which has been etched from a tube with a series of staggered slits.
Figure 5:
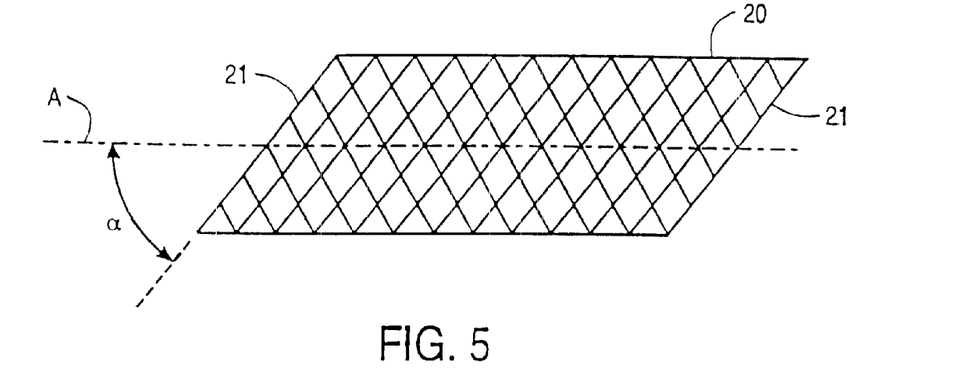
FIG. 5 is a schematic illustration of the intraluminal prosthesis of FIG. 4 which has been expanded to an expanded mode.

Referring now to FIGS. 4 and 5, a particularly preferred embodiment of the present invention having continuous ends will be described. The tubular member 20 is formed in the compressed mode, as seen in FIG. 4. The tubular member will be in an expanded configuration when implanted in a body lumen, as seen in FIG. 2. The prosthesis 20 is shown isolated in the expanded configuration in FIG. 5.

A method for forming the tubular member 20 in the present invention may be described with reference to FIG. 4. A tube of the desired material, optionally a resilient material such as nickel titanium alloy having a phase transformation temperature significantly below 37° C., preferably between 30° C. and 32° C., is obtained. The tube will have dimensions roughly equal to the desired dimensions of the tubular member when in the compressed mode. The tube may be drawn, rolled, or otherwise treated to achieve the desired wall thickness, diameter, and the like. Suitable wall thicknesses are in the range of about 0.1 mm to 0.5 mm. A staggered pattern of axial slots 25 is then formed in the tube, as illustrated in FIG. 4, which do not intersect the ends of the tube 21. The slots may be formed by electrical discharge machining (EDM), photochemical etching, laser cutting, machining or other conventional techniques. After the slots have been formed, the tube is mechanically expanded to its desired expanded (relaxed) diameter and heat treated at a suitable temperature to set the tube in the expanded mode, as shown in FIG. 5.

Alternatively, the tube may be formed of a malleable material such as 316 L stainless steel. The tube is again formed in the compressed mode, as described above. However, the slotted tube need not be expanded until positioned within the body lumen. In either case, sharp edges are removed by conventional techniques, such as deburring, abrasive extrusion, or the like. The result of the expansion is again the tubular member 20 illustrated in FIG. 5.

As seen in FIG. 5, the ends 21 of the expanded tubular member 20 present a continuous surface, having no openings or gaps. Although the present invention does not require that the ends be planar, straight ends 21 more directly define the oblique angle α, as discussed above. Furthermore, the even pattern at the end 21 of prosthesis 20 avoids the cantilevered diamond-shaped elements common in prostheses having perpendicular ends (see e.g., FIG. 1). The even end pattern of end 21 poses a lower risk of tissue damage, including puncture of the body lumen, than stents or grafts having cantilevered elements. This design can also minimize irritation and hyperplasic response resulting from placement of the tube.

Figure 6:
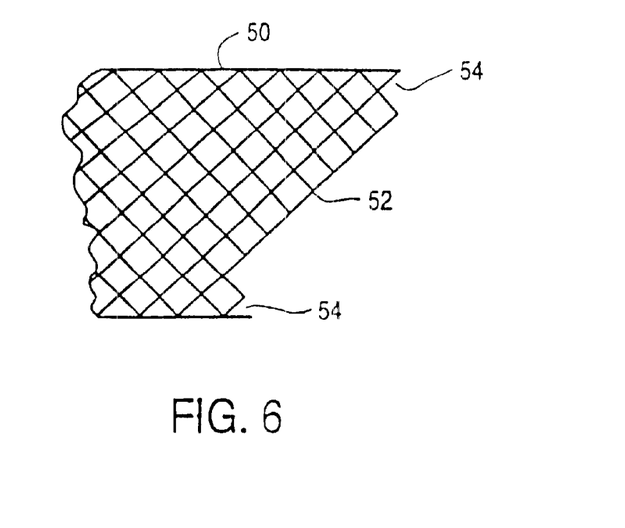
FIG. 6 is a schematic illustration of an embodiment of the present invention having continuous sides and cantilevered elements at the top and bottom.

Referring now to FIG. 6, a further embodiment of the present invention comprises a tubular prosthesis 50 having ends which are partially even. The ends are in part formed having continuous sides 52, and in part, preferably at a top and bottom portion, are formed having cantilevered diamond-shaped elements 54. Thus, the continuous sides 52 provide the reduced stenosis of the present invention, while the diamond-shaped elements can be biased outward to anchor prosthesis 50 in a body lumen.

Figure 7:
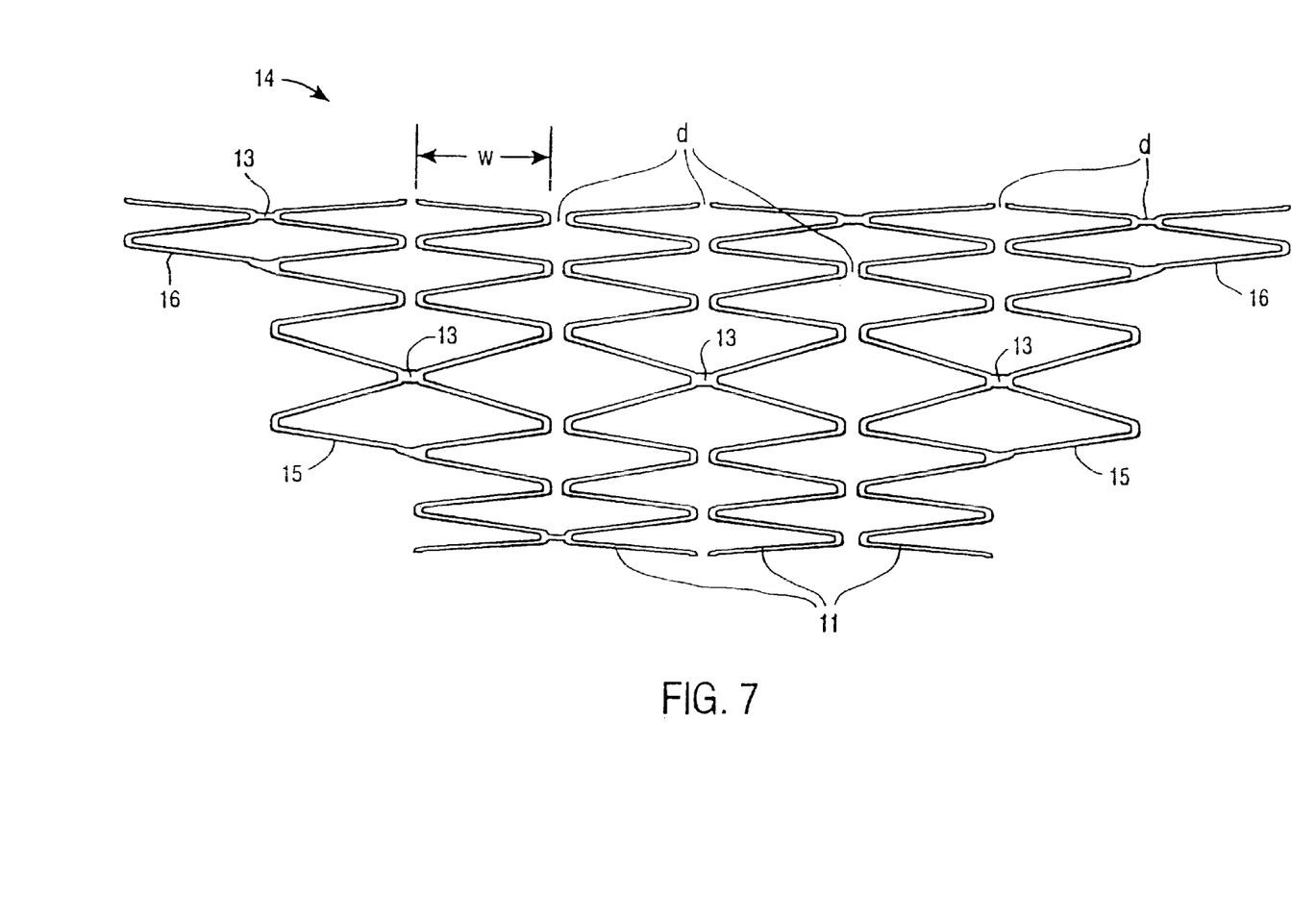
FIGS. 7 and 8 are side views of an alternative embodiment intraluminal prostheses according to the present invention.
Figure 8:
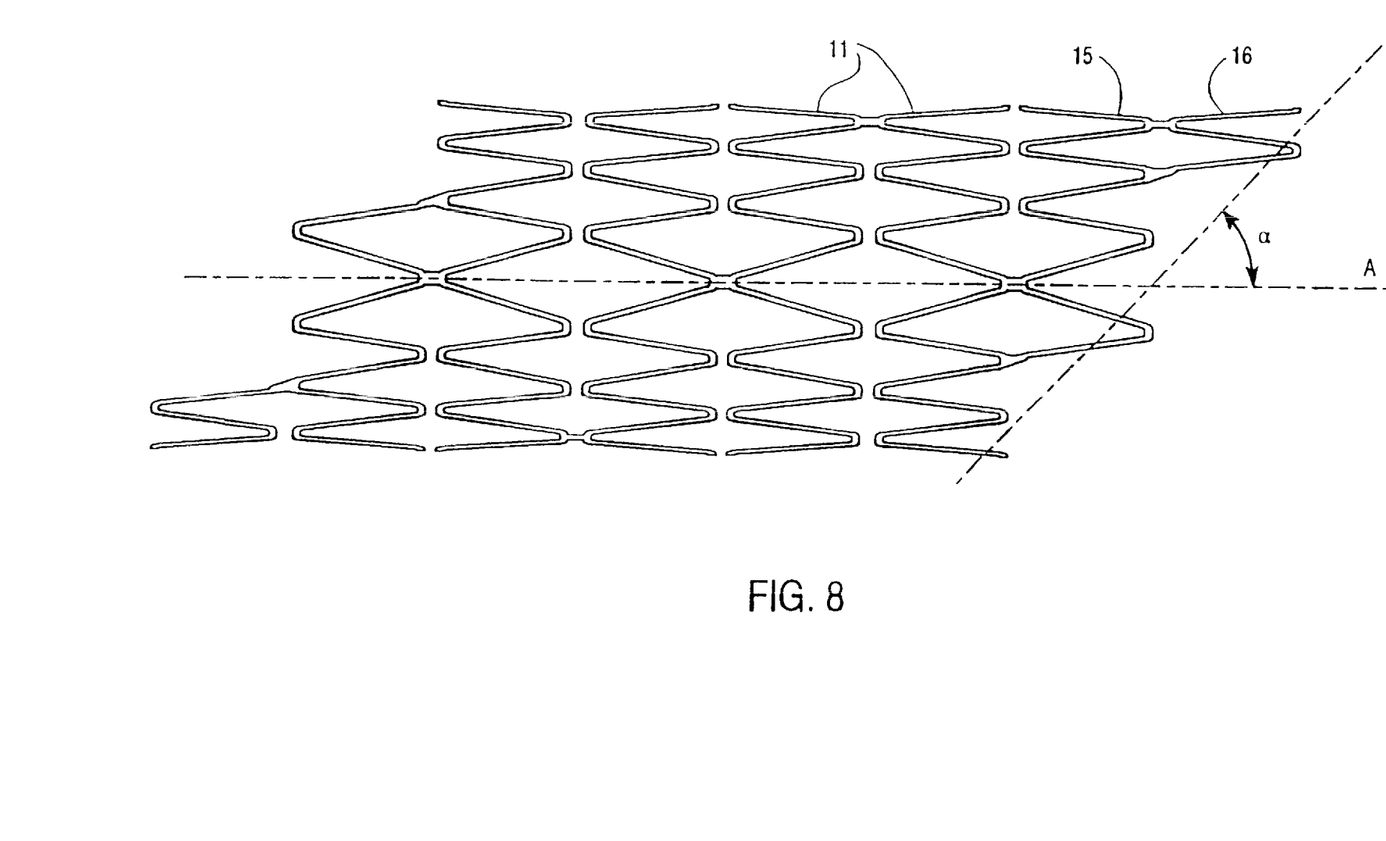

FIGS. 7 and 8 are side views of prostheses according to the present invention employing an alternative embodiment of the tubular member. Tubular member 14 has ends which are uneven. As can be seen in FIG. 8, the terminal ends of tubular member 14 are defined by a series of structural members having staggered lengths. Specifically, a plurality of band members 11 are joined to at least one transition member 15, which in turn is joined to at least one end member 16. These structural members form an oblique angle α to the axis A of the lumen.

As shown in FIG. 7, the radially compressible band members 11 each comprises a zig-zag or Z-shaped element forming a continuous circular ring. Each band member 11 will have a width w in the range from 2 mm to 15 mm, and the tubular frame will comprise from 1 to 30 individual band members. Adjacent band members 11 are spaced-apart from each other by a short distance d and are joined by bridge elements 13. Flexibility is enhanced by providing only two diametrically opposed bridge elements 13 between each adjacent pair of band members 11.

As can be seen in FIG. 7, the oblique ends of the tubular member need not be formed parallel to each other. The ends may angle in the same direction, as in FIG. 8, they may be opposed, as in FIG. 7, or they may further be at some skew angle (not shown). Although the present prostheses preferably have angles at both ends, space limitations or other considerations may dictate that one end of an intraluminal prosthesis be perpendicular to the flow. Thus the present invention also provides that only a single end may be oblique, thereby reducing stenoses associated with intraluminal prostheses where possible.

Figure 9A:
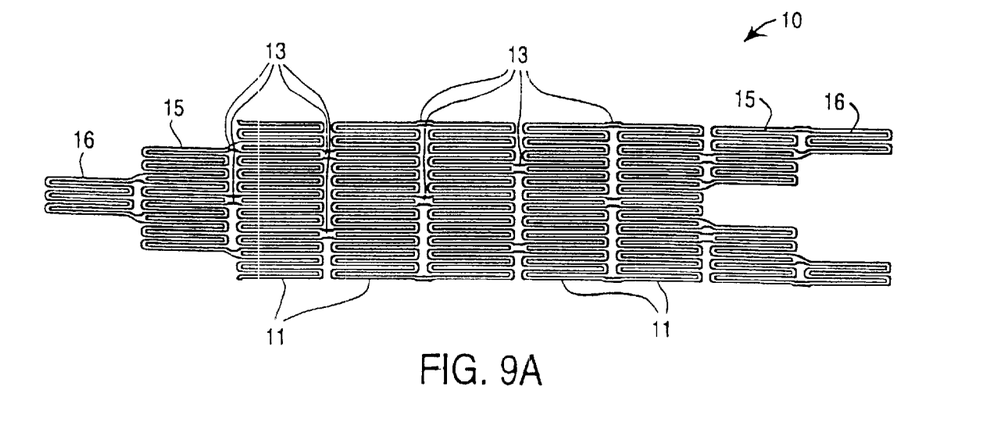
FIGS. 9A and 9B are schematic illustrations showing a joining pattern for radially compressible band members used to form the intraluminal prosthesis of FIG. 8.
Figure 9B:
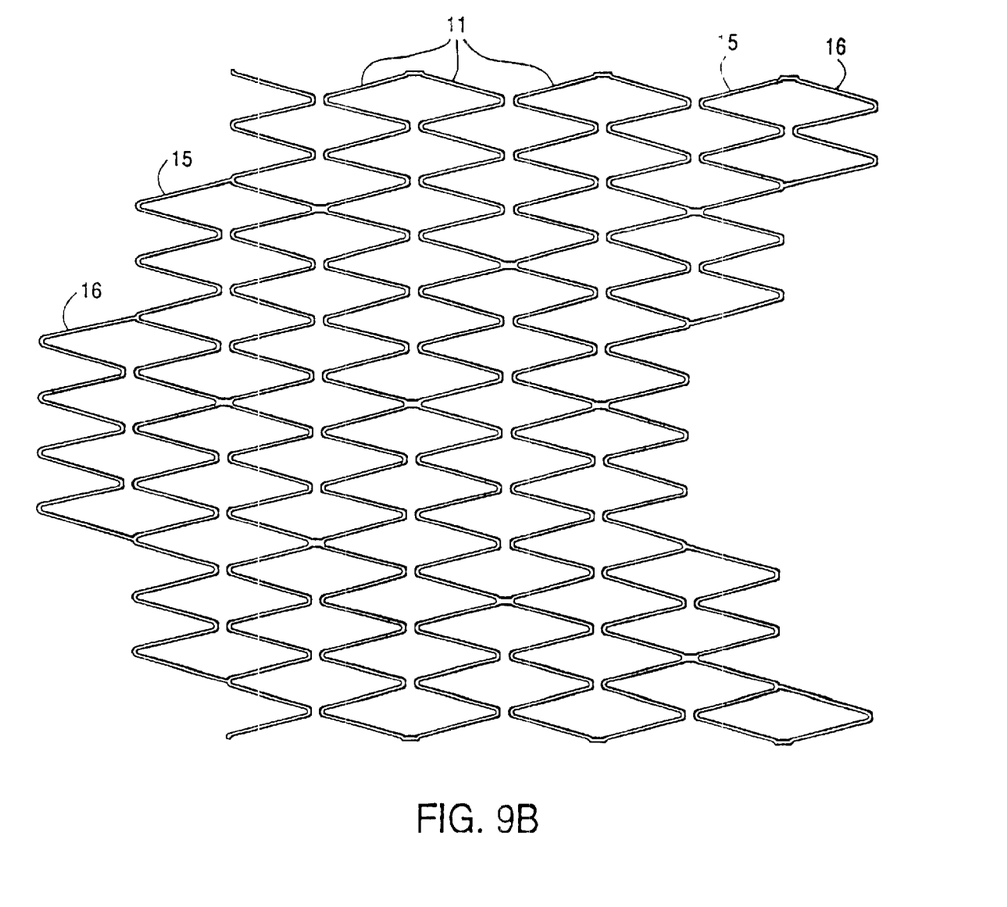

A joining pattern of adjacent band members 11 is illustrated in FIGS. 9A and 9B. FIG. 9A illustrates the tubular member 14 as it would look if unrolled onto a flat surface. FIG. 9B is similar to FIG. 9A, except that the band members are expanded. The expansion is shown at 30°, but will frequently extend up to 60° or higher in use.

Figure 10:
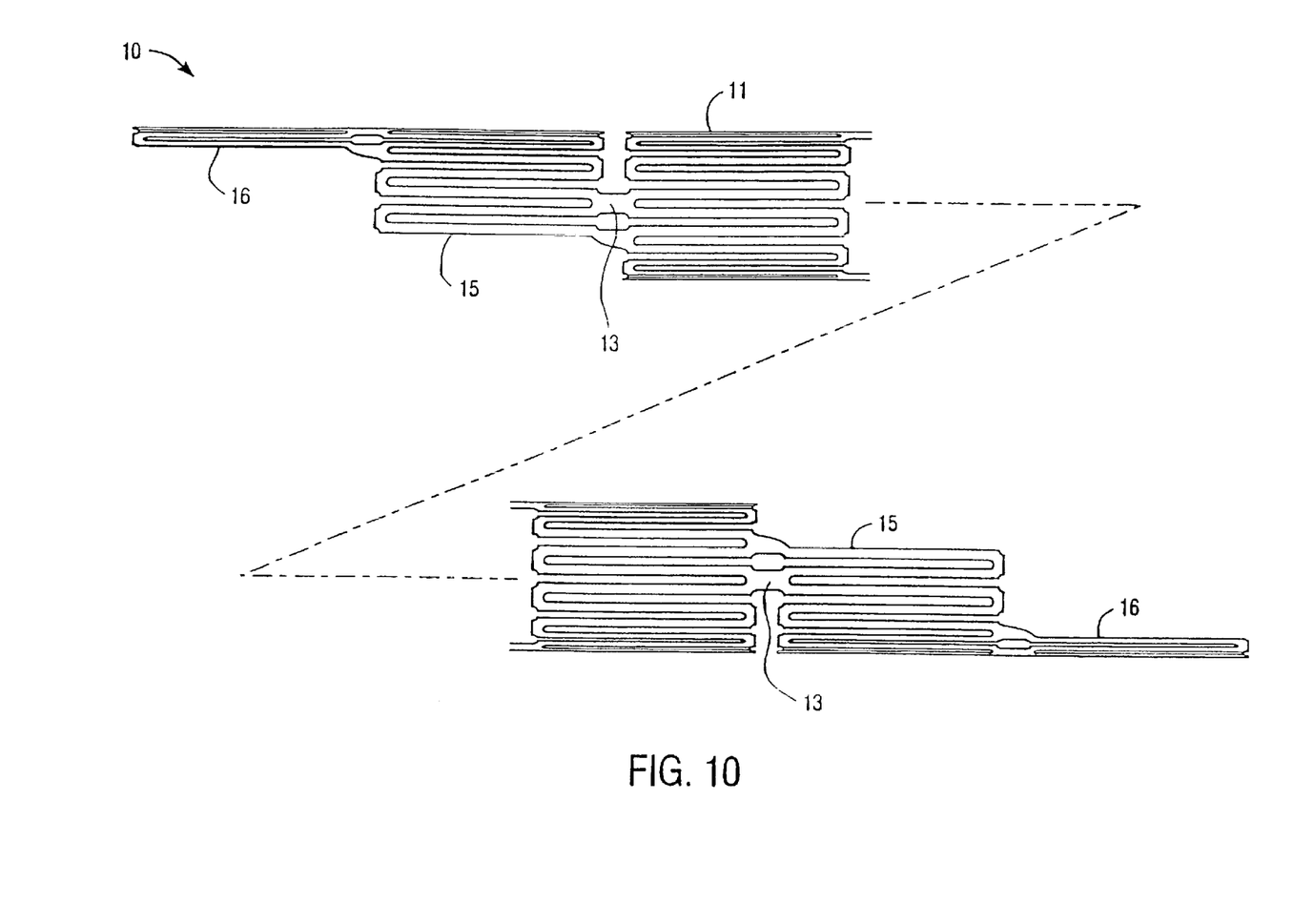
FIG. 10 illustrates a structure which has been etched from a tube and which may be subsequently expanded to form the intraluminal prosthesis of FIG. 8.

Referring now to FIG. 10, the tubular member 14 may be formed by a method similar to that described for the tubular member 20, as discussed in regard to FIGS. 4 and 5. Tubular member 14 may again be formed of a malleable material or a resilient material, as described above. In either case, a pattern of axial and circumferential slots are cut into the tube, as shown. It should be recognized that prostheses formed by the method of tubular member 14 may also have continuous ends or sides, where a sufficient number of transition bands 15 are provided, and where the angle of expansion is the same as the oblique end angle.

Figure 11:
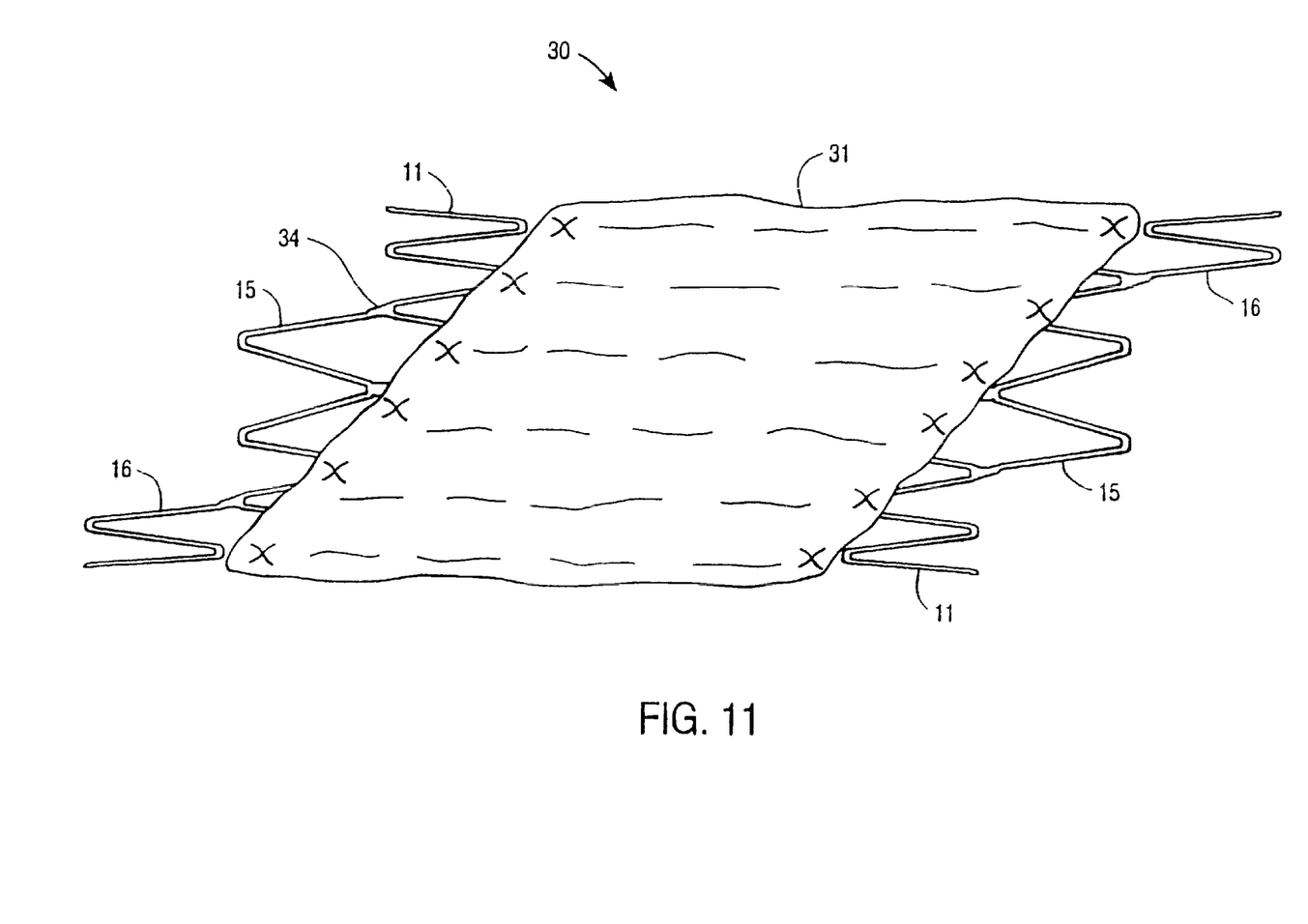
FIG. 11 is an illustration of a intraluminal graft according to the present invention.
Figure 12:
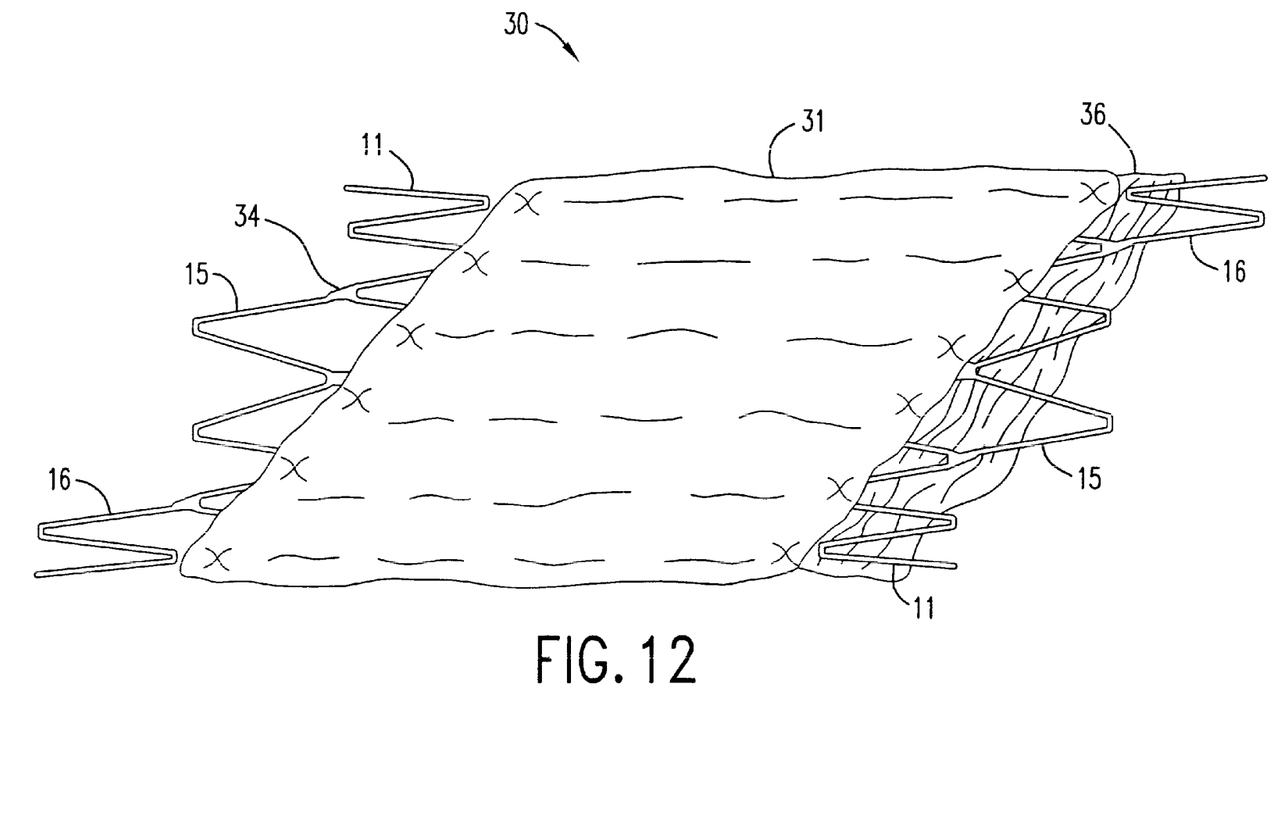
FIG. 12 is an illustration of an intraluminal graft having a second liner according to the present invention.

A further embodiment of the present invention is shown in FIG. 11. FIG. 11 illustrates an intraluminal graft having oblique ends. A perforate tubular frame 34 comprises a plurality of bands 11, as was described above in regard to the tubular member of FIG. 7. End bands 16 and transition bands 15 form an oblique angle with the axis of the lumen of graft 30. Additionally, a liner 31 covers at least a portion of the outside of the graft, thereby substantially sealing the perforations of the tubular frame over the covered portion. The liner is sutured to the frame 34, preferably so that the ends of the liner 31 are angularly aligned with the respective ends of the frame 34. The ends may optionally be fully aligned with ends of the graft, i.e., the liner 31 may extend to the ends of the perforate tubular frame. The design may reduce the proliferation of hyperplasic cells. In an alternate embodiment, as shown in FIG. 12, a second liner 36 covers at least a portion of the inside of the graft.

The liner(s) will be composed of conventional biological graft materials, such as polyesters, polytetrafluoroethylenes (PTFE's), polyurethanes, and the like, usually being in the form of woven fabrics, non-woven fabrics, polymeric sheets, membranes, and the like.

The liner 31 will be attached to the tubular frame and will cover at least a portion of one of the major surfaces of the tubular frame: the interior surface of the lumen, the exterior surface of the frame, or both. For example, the liner 31 may be stitched or otherwise secured to the tubular frame along a plurality of circumferentially spaced-apart axial lines.

Such attachment permits the liner 31 to fold along a plurality of axial fold lines when the frame is radially compressed. The liner 31 will further be able to open and conform to the luminal wall of the tubular frame as the frame expands. Alternatively, when inner and outer liners 31,36 are used, the liners may be stitched, heat welded, or ultrasonically welded together to sandwich the tubular frame therebetween.

The liner 31 will preferably be circumferentially sealed against the tubular frame at least one end, preferably at both ends. It is also preferred in some cases that the ends of the perforate tubular frame be exposed, i.e., not covered by the liner material, typically over a length in the range from about 1 mm to 25 mm. Frame which is not covered by the liner permits blood perfusion through the perforations and into branch arteries such as the renal arteries in the case of abdominal aorta grafts, while providing additional area for anchoring the frame against the blood vessel lumen.

Although the foregoing invention has been described in some detail by way of illustration and example, for purposes of clarity of understanding, it will be obvious that certain changes and modifications may be practiced within the scope of the appended claims.

What is claimed is:

1. An intravascular prosthesis comprising a tubular member having a proximal end, a distal end, a lumen, and luminal axis, wherein the tubular member is formed of a plurality of band members and is insertable within a blood vessel in a small diameter configuration, and is expandable within the blood vessel to an expanded diameter configuration forming a lumen having a substantially uniform cross section perpendicular to said luminal axis from said distal end to said proximal end of said tubular member, and wherein at least one of the proximal end and the distal end has a terminal edge which is disposed substantially at an oblique angle relative to the luminal axis so that the terminal edge continuously contacts a surrounding blood vessel wall along an oblique cross section when expanded therein.

2. An intravascular prosthesis as in claim 1, wherein at least a portion of the tubular member is composed of a malleable material.

3. An intravascular prosthesis as in claim 1, wherein at least a portion of the tubular member is composed of a resilient material.

4. An intravascular prosthesis as in claim 1, wherein the oblique angle is in the range between 20° and 80°.

5. An intravascular prosthesis as in claim 1, wherein at least one of the terminal edges defines an oblique angle at least in part as a series of staggered steps.

6. An intravascular prosthesis as in claim 1, wherein the intravascular prosthesis is configured for insertion of a balloon catheter into the intravascular prosthesis for expanding the intravascular prosthesis by inflating the balloon catheter, the intravascular prosthesis remains expanded after removal of the balloon catheter.

7. An intravascular prosthesis as in claim 1, wherein the intravascular prosthesis is restrained in a radially compressed mode prior to positioning, and released at the target location.

8. An intravascular prosthesis as in claim 1, wherein the intravascular prosthesis is configured for insertion of a balloon catheter into at least one end of the intravascular prosthesis for expanding the at least one end of the intravascular prosthesis by inflating the balloon catheter, wherein during expansion a middle portion of the intravascular prosthesis is restrained in a radially compressed mode prior to positioning and releasing the middle portion at a target location.

9. An intraluminal graft comprising:

a perforate tubular frame having a proximal end, a distal end, a lumen, and a luminal axis; and a first liner which covers at least a portion of a first surface of the tubular frame, wherein the tubular frame is formed of a plurality of band members and is insertable within a body lumen in a small diameter configuration, and is expandable within the body lumen to an expanded diameter configuration, and wherein the proximal end and the distal end of the tubular frame each have terminal edges which are disposed substantially at an oblique angle relative to the luminal axis so that each terminal edge continuously contacts a surrounding luminal wall along an oblique cross section when expanded therein.

10. An intraluminal graft as in claim 9, wherein the proximal end of the first liner and a distal end of the first liner are angularly aligned with the proximal end of the tubular frame and the distal end of the tubular frame, respectively.

11. An intraluminal graft as in claim 9, wherein the proximal end of the first liner and a distal end of the first liner are fully aligned with the proximal end of the tubular frame and the distal end of the tubular frame, respectively.

12. An intraluminal graft as in claim 9, wherein the liner is tied to the tubular frame.

13. An intraluminal graft as in claim 9, wherein at least a portion of the tubular member is composed of a malleable material.

14. An intraluminal graft as in claim 9, wherein at least a portion of the tubular member is composed of a resilient material.

15. An intraluminal graft as in claim 14, wherein the tubular frame is adapted to resiliently expand to the expanded mode when placed within the body lumen.

16. An intraluminal graft as in claim 9, further comprising a second liner disposed over at least a portion of a second surface of the tubular frame.

17. An intraluminal graft as in claim 16, wherein the second liner is welded to the first liner.

18. An intraluminal graft as in claim 9, wherein at least one of the terminal edges defines an oblique angle at least in part as a series of staggered steps.

19. An intraluminal graft comprising:

a perforate tubular frame having a proximal end, a distal end, a lumen, and a luminal axis; and a first liner which covers at least a portion of a first surface of the tubular frame, wherein the tubular frame insertable within a body lumen in a small diameter configuration, and is expandable within the body lumen to an expanded diameter configuration, wherein the proximal end and the distal end of the tubular frame each have terminal edges which are disposed substantially at an oblique angle relative to the luminal axis so that each terminal edge continuously contacts a surrounding luminal wall along an oblique cross section when expanded therein, and wherein at least one of the proximal end and the distal end defines a series of cantilevered elements.

* * * * *